United States Patent
Lutz et al.

(10) Patent No.: US 9,549,767 B2
(45) Date of Patent: *Jan. 24, 2017

(54) ENCAPSULATED SCREW LOCKING SYSTEM

(71) Applicant: Stryker European Holdings I, LLC, Kalamazoo, MI (US)

(72) Inventors: Christian Lutz, Mönkeberg (DE); Tim Bargen, Kiel (DE)

(73) Assignee: Stryker European Holdings I, LLC, Kalamazoo, MI (US)

( * ) Notice: Subject to any disclaimer, the term of this patent is extended or adjusted under 35 U.S.C. 154(b) by 274 days.

This patent is subject to a terminal disclaimer.

(21) Appl. No.: 13/861,802

(22) Filed: Apr. 12, 2013

(65) Prior Publication Data

US 2013/0231610 A1 Sep. 5, 2013

Related U.S. Application Data

(63) Continuation of application No. 12/640,780, filed on Dec. 17, 2009, now Pat. No. 8,435,239.

(51) Int. Cl.
*A61B 17/56* (2006.01)
*A61B 17/72* (2006.01)
(Continued)

(52) U.S. Cl.
CPC ........... *A61B 17/72* (2013.01); *A61B 17/7233* (2013.01); *A61B 17/00491* (2013.01);
(Continued)

(58) Field of Classification Search
CPC . A61B 17/72; A61B 17/7233; A61B 17/7241; A61B 17/8047; A61B 19/026
(Continued)

(56) References Cited

U.S. PATENT DOCUMENTS

| 4,514,125 A | 4/1985 | Stol |
| 4,919,666 A | 4/1990 | Buchhorn et al. |

(Continued)

FOREIGN PATENT DOCUMENTS

| CN | 86209770 U | 11/1987 |
| CN | 1081872 A | 2/1994 |

(Continued)

OTHER PUBLICATIONS

Chinese Office Action with Search Report for Application No. 201010599704.7 dated Aug. 1, 2012.

(Continued)

*Primary Examiner* — Mary Hoffman
*Assistant Examiner* — Tara R Carter
(74) *Attorney, Agent, or Firm* — Lerner, David, Littenberg, Krumholz & Mentlik, LLP (57) ABSTRACT

The present invention discloses a system for securing at least one fastener to an implant. At least one adhesive capsule is inserted in a recess preferably located along a longitudinal axis of the implant. The at least one adhesive capsule may be inserted in the recess and held in place therein by a holder. A plurality of adhesive capsules and holders may be inserted in one or more recesses located substantially along the longitudinal axis of the implant. The at least one adhesive capsule preferably has a casing housing an adhesive material configured to be pierced by the at least one fastener to secure the at least one fastener to an aperture of the implant. The casing of the adhesive capsule may form an annular passageway to receive a guide wire for aiding the insertion of the capsule in an implant having a longitudinal bore along at least a portion thereof.

19 Claims, 8 Drawing Sheets

(51) Int. Cl.
*A61B 17/00* (2006.01)
*A61B 17/74* (2006.01)
*A61B 17/84* (2006.01)
*A61F 2/30* (2006.01)

(52) U.S. Cl.
CPC ......... *A61B 17/7241* (2013.01); *A61B 17/744* (2013.01); *A61B 17/846* (2013.01); *A61F 2002/30448* (2013.01); *A61F 2220/005* (2013.01); *Y10T 29/49966* (2015.01)

(58) Field of Classification Search
USPC ............ 606/62–68, 300, 304, 309–318, 323;
411/82–82.3, 258, 930; 623/17.12, 20.16,
623/20.17, 23.13, 23.34, 23.48, 23.75
See application file for complete search history.

(56) References Cited

U.S. PATENT DOCUMENTS

| | | | |
|---|---|---|---|
| 5,084,050 A | | 1/1992 | Draenert |
| 5,433,718 A * | | 7/1995 | Brinker .......... 606/62 |
| 5,618,286 A | | 4/1997 | Brinker |
| 5,681,289 A | | 10/1997 | Wilcox et al. |
| 5,756,127 A | | 5/1998 | Grisoni et al. |
| 5,776,194 A | | 7/1998 | Mikol et al. |
| 6,048,343 A | | 4/2000 | Mathis et al. |
| 6,296,645 B1 * | | 10/2001 | Hover et al. .......... 606/62 |
| 6,409,972 B1 | | 6/2002 | Chan |
| 6,517,563 B1 * | | 2/2003 | Paolitto et al. .......... 606/205 |
| 6,565,572 B2 | | 5/2003 | Chappius |
| 6,679,890 B2 | | 1/2004 | Margulies et al. |
| 6,709,436 B1 | | 3/2004 | Hover et al. |
| 6,783,529 B2 | | 8/2004 | Hover et al. |
| 6,786,908 B2 | | 9/2004 | Hover et al. |
| 6,808,527 B2 * | | 10/2004 | Lower et al. .......... 606/62 |
| 7,160,302 B2 | | 1/2007 | Warburton |
| 7,488,320 B2 | | 2/2009 | Middleton |
| 7,527,611 B2 * | | 5/2009 | Sweeney .......... 604/264 |
| 8,377,062 B2 * | | 2/2013 | Lutz .......... A61B 17/72 606/62 |
| 2001/0021852 A1 | | 9/2001 | Chappius |
| 2002/0029041 A1 | | 3/2002 | Hover et al. |
| 2002/0173792 A1 | | 11/2002 | Severns et al. |
| 2003/0083662 A1 | | 5/2003 | Middleton |
| 2004/0097930 A1 | | 5/2004 | Justis et al. |
| 2004/0158252 A1 | | 8/2004 | Prager et al. |
| 2004/0180072 A1 | | 9/2004 | Tunc et al. |
| 2005/0149022 A1 | | 7/2005 | Shaolian et al. |
| 2006/0229617 A1 | | 10/2006 | Meller et al. |
| 2006/0247642 A1 | | 11/2006 | Stone et al. |
| 2007/0083265 A1 | | 4/2007 | Malone |
| 2007/0265704 A1 | | 11/2007 | Mayer et al. |
| 2008/0021474 A1 | | 1/2008 | Bonutti et al. |
| 2008/0039845 A1 | | 2/2008 | Bonutti et al. |
| 2008/0039854 A1 | | 2/2008 | Rabiner |
| 2008/0287949 A1 | | 11/2008 | Keith et al. |
| 2009/0024161 A1 | | 1/2009 | Bonutti et al. |
| 2009/0157078 A1 | | 6/2009 | Mikol |
| 2009/0164016 A1 | | 6/2009 | Georgy et al. |
| 2009/0204117 A1 | | 8/2009 | Middleton |

FOREIGN PATENT DOCUMENTS

| | | | |
|---|---|---|---|
| CN | 1826086 A | 8/2006 | |
| CN | 201263717 Y | 7/2009 | |
| CN | 102100943 A | 6/2011 | |
| WO | 8801160 A1 | 2/1988 | |
| WO | 9403143 A1 | 2/1994 | |
| WO | 97/17032 A1 | 5/1997 | |
| WO | 98/46169 A1 | 10/1998 | |
| WO | WO9846169 * | 10/1998 | ............... A61F 2/28 |
| WO | 01/39812 A1 | 6/2001 | |
| WO | 03/105698 A2 | 12/2003 | |
| WO | 2004/096067 A2 | 11/2004 | |
| WO | 2005020830 A1 | 3/2005 | |
| WO | 2006/044490 A2 | 4/2006 | |

OTHER PUBLICATIONS

European Search Report, EP 10194802, dated Jun. 8, 2011.
European Search Report, EP 10194804, dated Mar. 10 11, 2011.
Partial European Search Report, EP 10194802, dated Apr. 11, 2011.

* cited by examiner

ENCAPSULATED SCREW LOCKING SYSTEM

CROSS-REFERENCE TO RELATED APPLICATIONS

The present application is a continuation of U.S. patent application Ser. No. 12/640,780, filed Dec. 17, 2009, the disclosure of which is incorporated herein by reference.

FIELD OF THE TECHNOLOGY

The present invention relates to a fastener locking system and method for securing a fastener, such as a bone screw to an orthopedic implant, such as an intramedullary nail. In particular, the present invention relates to providing an adhesive capsule adjacent a fastener receiving aperture in the implant and piercing the capsule with a fastener such that adhesive material inside the capsule secures the fastener in an aperture of the implant.

BACKGROUND OF THE INVENTION

Orthopedic implants, such as intramedullary nails are used in fracture fixation. Prior to inserting an intramedullary nail in the canal of a femur, a bore is generally first created. The bore may be created with a reamer, for example. Once the nail is positioned within the canal of the femur, it is generally secured in place by fasteners, such as locking nails or screws. Such fasteners are generally first inserted through a portion of a patient's bone, such as the femur, and then through a fastener receiving aperture located along the length of the nail. Locking features on the fastener itself, on the nail, or other structures such as locking inserts may be used to secure the fastener in the aperture of the nail.

The backing-out of fasteners, such as screws, in implants has been addressed in patent references. U.S. Pat. No. 7,247,157 teaches a ring for securing an interlocking screw in an implant. In one embodiment, there is shown a bone nail having an implant body including at least one bore with a threaded portion and a bone screw which engages the thread when it is threaded into a bone for the fixation of the implant body. The threaded bore of the implant body has an annular groove, the diameter of which is larger than the thread outer diameter, and which receives a ring of a deformable material with an inner diameter which is smaller than the outer diameter of the thread of the bone screw so that the ring extends partially into the bore.

BRIEF SUMMARY OF THE INVENTION

A first aspect of the present invention is an adhesive capsule including a longitudinally extending exterior wall having a first end and a second end. The longitudinally extending interior wall is preferably spaced from the exterior wall and the interior wall has a first end and a second end. The first and second ends of the exterior and interior walls are preferably sealed and the sealed exterior and interior walls define an enclosed chamber. The adhesive capsule includes an adhesive contained within the enclosed chamber. The interior wall preferably forms a passageway along a length of the adhesive capsule and through the first and second ends of the interior wall.

In accordance with one embodiment of this first aspect of the present invention, the enclosed chamber containing the adhesive includes a first longitudinal section and a second longitudinal section separated by a barrier wall such that the adhesive in the first section is separated from the adhesive in the second section.

In accordance with another embodiment of this first aspect of the present invention, the barrier wall is located at an intermediate portion along the length of the adhesive capsule.

In accordance with yet another embodiment of this first aspect of the present invention, the exterior wall has a circumferential ridge that extends outwardly therefrom.

In accordance with still yet another embodiment of this first aspect of the present invention, the exterior and interior walls are substantially cylindrical and the passageway is substantially cylindrical such that the enclosed chamber is annular.

In accordance with still yet another embodiment of this first aspect of the present invention, the first and second ends comprise a first end wall, and a second end wall, wherein a first end of the annular chamber is sealed by the first end wall and a second end of the annular chamber is sealed by the second end wall.

A second aspect of the present invention is a bone nail including an elongate shaft having a longitudinal bore at least partially therethrough and first and second bone screw receiving apertures. Preferably, the apertures each extend transverse to the longitudinal bore. Preferably, an adhesive capsule is positioned within the bore and communicates with both the first and second apertures.

In accordance with one embodiment of this second aspect of the present invention, the bone nail further includes a holder adapted to be received within the longitudinal bore of the elongate shaft, the holder adapted to receive an adhesive capsule therein and position the capsule at least partially within at least one of the first and second apertures.

In accordance with another embodiment of this second aspect of the present invention, the holder has a first and a second end, each end having a recess for holding an adhesive capsule to position a capsule at least partially within the first and the second apertures.

In accordance with yet another embodiment of this second aspect of the present invention, the longitudinal bore of the elongate shaft is threaded adjacent the nail aperture and the holder is threaded and adapted to threadingly engage the longitudinal bore of the elongate shaft.

In accordance with still yet another embodiment of this second aspect of the present invention, the bone nail includes a first adhesive capsule, and a second adhesive capsule, wherein the holder is adapted to receive both first and second adhesives capsules therein and position the first capsule at least partially within the first aperture and the second capsule at least partially within the second aperture.

A third aspect of the present invention is a bone nail including an elongate shaft having a longitudinal bore and at least one aperture extending transverse to the longitudinal bore. Preferably, an adhesive capsule is positioned within the bore, and a holder is adapted to be received within the bore, the holder having at least one recess adapted to receive the adhesive capsule and position the capsule at least partially within the at least one aperture.

In accordance with one embodiment of this third aspect of the present invention, the holder is cylindrical. Preferably, the holder is threaded and adapted to threadingly engage the longitudinal bore of the elongate shaft.

In accordance with another embodiment of this third aspect of the present invention, the bone nail has first and second transverse apertures and the holder is positioned within the longitudinal bore such that the holder communicates with the first and second transverse apertures, the holder having first and second recesses each adapted to receive an adhesive capsule.

In accordance with another embodiment of this third aspect of the present invention, a first adhesive capsule is positioned at least partially within the first transverse aperture and the second adhesive capsule is positioned at least partially within the second transverse aperture.

A fourth aspect of the present invention is a method for securing a fastener to an implant. The method includes positioning the implant adjacent bone, the implant having at least one aperture for receiving an elongate fastener therein and an internal recess communicating with the aperture. The method further includes placing an adhesive capsule within the internal recess, the adhesive capsule extending at least partially into the at least one aperture, the adhesive capsule having a casing housing an adhesive, the casing configured to be pierced by an elongate fastener. The method further includes inserting the fastener through the at least one aperture, piercing the adhesive capsule with at least a portion of the fastener, wherein the adhesive secures the elongate fastener to the implant.

In accordance with one embodiment of this third aspect of the present invention, the implant is an intramedullary nail.

In accordance with another embodiment of this third aspect of the present invention, the recess is a longitudinal bore extending at least partially along a length of the intramedullary nail.

In accordance with yet another embodiment of this third aspect of the present invention, the method further includes placing a retaining ring around the casing of the adhesive capsule prior to piercing the adhesive capsule with the fastener, the retaining ring configured to aid in maintaining the position of the adhesive capsule within the longitudinal bore of the intramedullary nail.

In accordance with still yet another embodiment of this third aspect of the present invention, the implant has a plurality of apertures adapted to each receive an elongate fastener therein and an internal recess communicating with each aperture. The method further includes placing an adhesive capsule within the internal recess communicating with each aperture, wherein each adhesive capsule extends at least partially into each aperture.

BRIEF DESCRIPTION OF THE DRAWINGS

A more complete appreciation of the subject matter of the present invention and the various advantages thereof can be realized by reference to the following detailed description in which reference is made to the accompanying drawings in which.

DETAILED DESCRIPTION

As used herein, when referring to bones or other parts of the body, the term "proximal" means closer to the heart and the term "distal" means more distant from the heart. The term "inferior" means toward the feet and the term "superior" means toward the head. The term "anterior" means toward the front part of the body or the face and the term "posterior" means toward the back of the body. The term "medial" means toward the midline of the body and the term "lateral" means away from the midline of the body.

Figure 1:
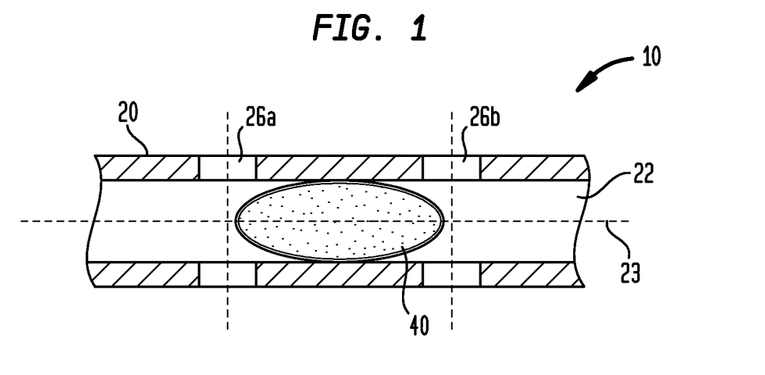
FIG. 1 is a cross-sectional view of an embodiment of a longitudinal bore of an intramedullary nail having an adhesive capsule located therein.
Figure 2:
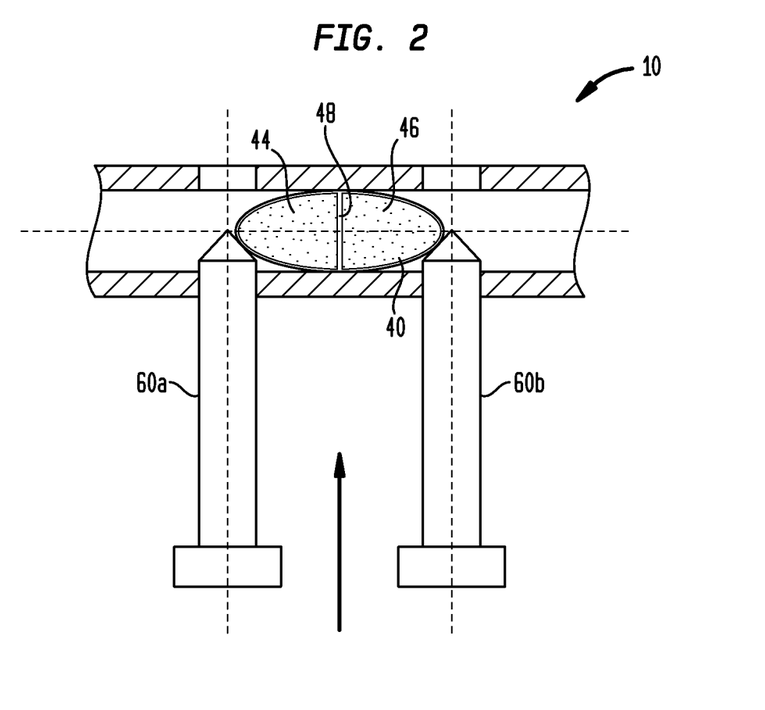
FIG. 2 is a cross-sectional view of the intramedullary nail shown in FIG. 1, with tips of two fasteners each located in an aperture of the intramedullary nail.
Figure 3:
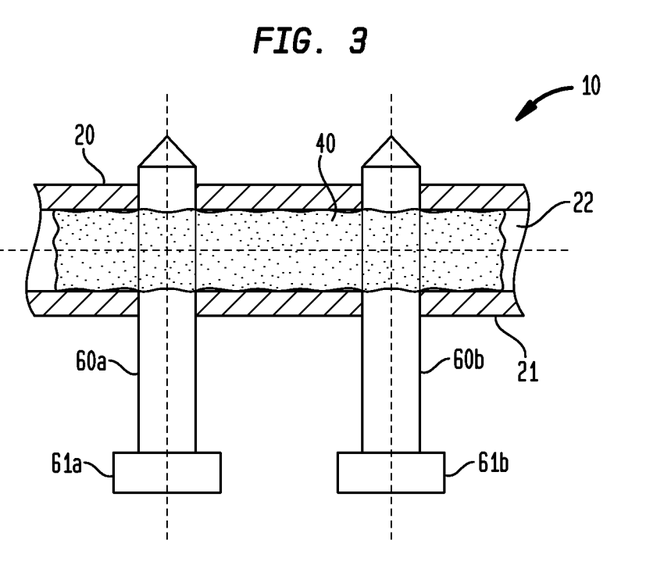
FIG. 3 is a cross-sectional view of the adhesive capsule, intramedullary nail, and two fasteners shown in FIG. 2, with the adhesive capsule having been pierced by the two fasteners.

Referring to the drawings, wherein like reference numerals represent like elements, there is shown in the figures, in accordance with embodiments of the present invention, a screw locking system, designated generally by reference numeral 10. FIGS. 1-3 refer to screw locking system 10. Preferably screw locking system 10 includes a portion of an intramedullary nail 20, at least one adhesive capsule 40, and at least one fastener 60. Two fasteners 60a, 60b are shown in FIGS. 2 and 3.

Intramedullary nail 20 is preferably an elongate shaft configured to be housed within a canal of a patient's femur. Preferably, intramedullary nail 20 includes a longitudinal bore 22 at least partially along a length thereof. Bore 22 is shown having an axis 23. While axis 23 is shown as a straight line in FIGS. 1-3, axis 23 may curve if a portion of the length of nail 20 is also curved. Nail 20 preferably further includes at least first and second bone screw receiving apertures 26a, 26b. Preferably, apertures 26a, 26b each extend transverse to longitudinal bore 22 of intramedullary nail 20.

Adhesive capsule 40 preferably includes an outer casing housing an adhesive material. The outer casing of the adhesive capsule is preferably thin such that it may easily be pierced by fasteners, such as fasteners 60*a*, 60*b*, for example. As shown in FIG. 1, adhesive capsule 40 forms a chamber for housing adhesive material therein. Alternatively, adhesive capsule may include two chambers 44, 46 as shown in FIG. 2, or more than two chambers. A barrier wall 48 separates adhesive of capsule 40 into first and second chambers 44, 46. Adhesive capsule 40 may further include more than one barrier wall 48 to form a plurality of chambers.

As shown in the embodiment of FIG. 2, adhesive capsule 40 is positioned within bore 22 and is communicating with both first and second apertures 26*a*, 26*b*. First chamber 44 and second chamber 46 of adhesive capsule 40 is separated by barrier wall 48. In this embodiment, first chamber 44 may be pierced by fastener 60A, for example, without second chamber 46 being pierced and vice versa.

As shown in FIG. 3, fasteners 60*a*, 60*b* have pierced adhesive capsule 40 such that adhesive material preferably surrounds a length of fasteners 60*a*, 60*b*. Preferably, fasteners 60*a*, 60*b* are received within apertures 26*a*, 26*b* until heads 61*a*, 61*b* of each fastener 60*a*, 60*b* is seated on an exterior surface of the patient's bone (not shown). Depending on the chemical and/or physical properties of the adhesive material located inside capsule 40, the adhesive material will eventually harden and secure fasteners 60*a*, 60*b* with respect to nail 20 and thus securing nail 20 with the canal of the patient's femur. Preferably, once the adhesive material has hardened, fasteners 60*a*, 60*b*, for example, are prevented from backing-out of nail 20. The hardened adhesive also aids in the angular stability of a fastener in an aperture of nail 20.

Figures 4, 4A:
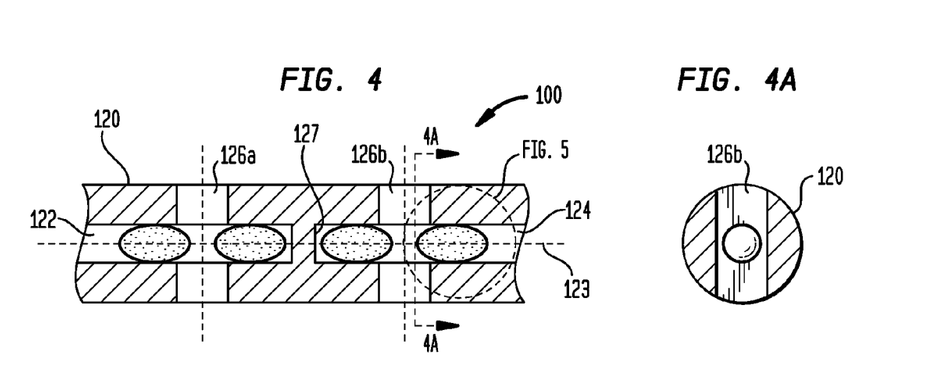
FIG. 4 is a cross-sectional view of an embodiment of an intramedullary nail, including a plurality of adhesive capsules each located in recesses adjacent apertures of the intramedullary nail.
FIG. 4A is a cross-sectional view of the intramedullary nail taken along line A-A of FIG. 4.
Figure 5:
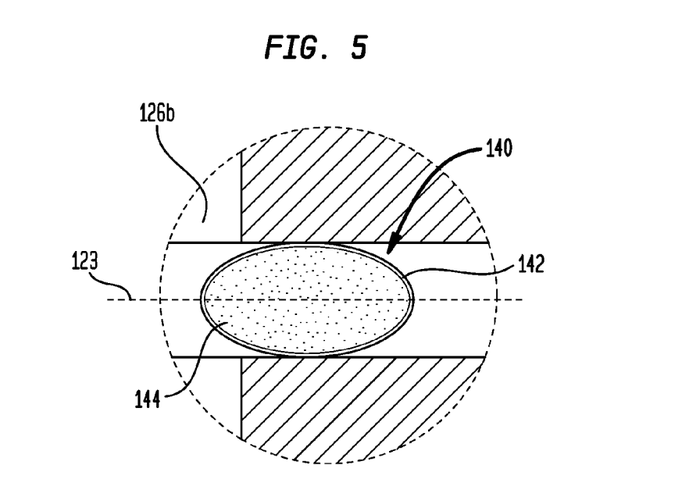
FIG. 5 is an embodiment of an adhesive capsule of the present invention.
Figure 6:
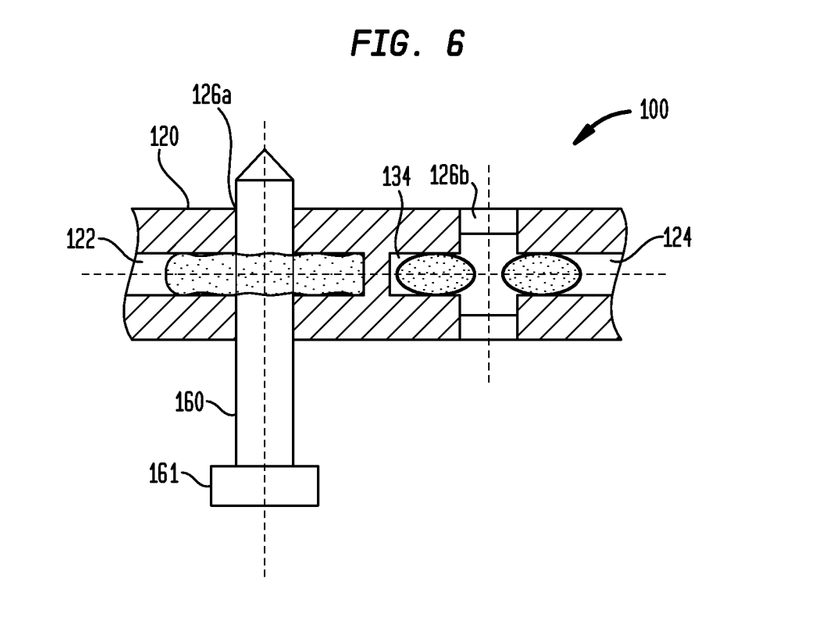
FIG. 6 is a cross-sectional view of the intramedullary nail shown in FIG. 4, with two of the plurality of adhesive capsules having been pierced by a fastener located in an aperture of the intramedullary nail.

FIGS. 4-6 refer to screw locking system 100. Preferably screw locking system 100 includes intramedullary nail 120, at least one adhesive capsule 140, and at least one fastener 160.

Intramedullary nail 120 is a preferably elongate shaft configured to be housed within a canal of a patient's femur. Preferably, intramedullary nail 120 includes at least two longitudinal recess or bores 122, 124 at least partially along a length thereof. In this embodiment, recess or bore 122 does not extend along a substantial length of nail 120, and is preferably interrupted by a wall 127 along the length of nail 120 separating recess 122 from recess 124. Preferably, each recess 122, 124 is shown having an axis 123. While axis 123 is shown as a straight line in FIGS. 4-6, axis 123 may curve if a portion of the length of nail 120 is also curved. Intramedullary nail 120 preferably further includes at least first and second bone screw receiving apertures 126*a*, 126*b*. Preferably, apertures 126*a*, 126*b* each extend transverse to longitudinal bore 122 of intramedullary nail 120.

Adhesive capsule 140 preferably includes an outer casing housing an adhesive material. The outer casing of the adhesive capsule is preferably thin such that it may easily be pierced by fasteners, such as fastener 160 for example. As shown in FIG. 5, adhesive capsule 140 forms chamber 144 for housing adhesive material therein. Alternatively, adhesive capsule 140 may include two or more chambers. A barrier wall may be used to separate the adhesive of capsule 140 into first and second chambers, for instance. Adhesive capsule 140 may further include more than one barrier wall to form a plurality of chambers.

As shown in FIG. 4, a plurality of capsules 140 are located in recesses 122, 124 of nail 120. Capsules 140 are located in recesses 122, 124 such that a portion of capsules 140 is located in fastener receiving apertures 126*a*, 126*b* of nail 120. FIG. 4A is a cross-sectional view showing capsule 140 located in recess 124, for example. FIG. 5 is a detailed view also showing capsule 140 located in recess 124, wherein a portion of capsule 140 is clearly shown located in fastener receiving apertures 126*b* of nail 120. Depending on the properties of the adhesive material in capsule 140 and the location of capsule 140 located in a fastener receiving aperture of nail 120 preferably determines how much adhesive will come in contact with a fastener that pierces capsule 140 in the fastener receiving aperture of nail 120.

As shown in FIG. 6, fasteners 160 has pierced adhesive capsule 40 in fastener receiving aperture 126*a* such that the adhesive material preferably surrounds a length of fastener 160. Preferably, fastener 160 is received within apertures 126*a*, 126*b* until a head 161 of fastener 160 is seated on the exterior surface of the patient's bone (not shown). Depending on the chemical and physical properties of the adhesive material, the adhesive material will eventually harden and secure fastener 160, for example, with respect to nail 120.

Figure 7:
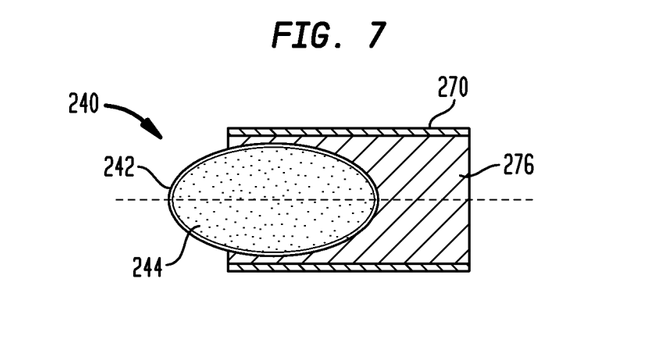
FIG. 7 is a cross-sectional view of an embodiment of a holder, including an adhesive capsule located partially within the holder.
Figure 8:
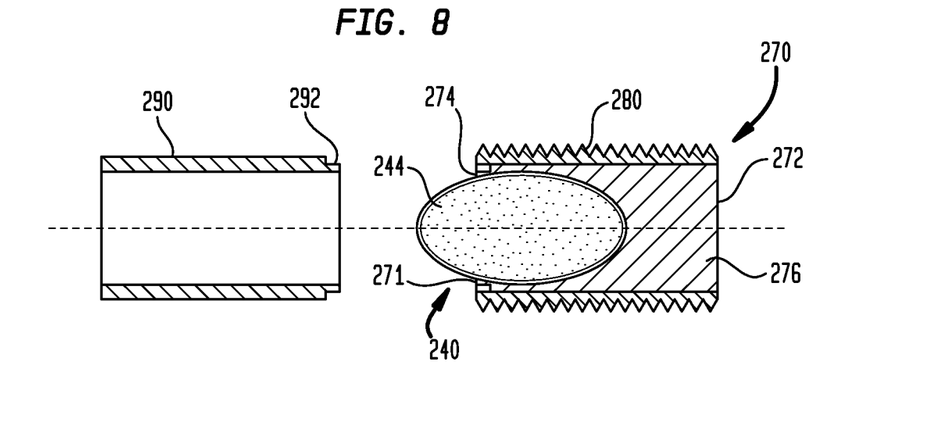
FIG. 8 is a cross-sectional view of the holder shown in FIG. 7, with an insertion instrument for engaging the holder.
Figure 8A:
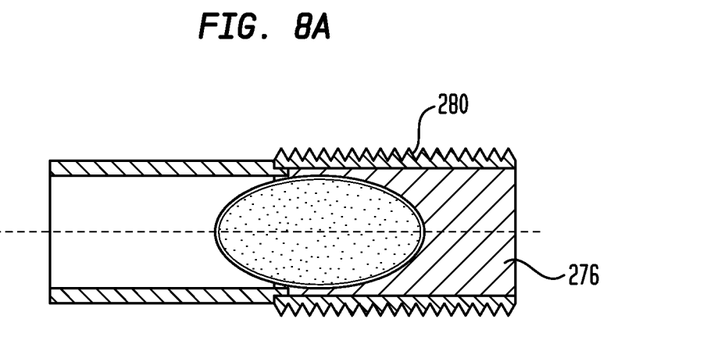
FIG. 8A is a view of the insertion instrument engaged to the holder shown in FIG. 8.
Figures 9, 10:
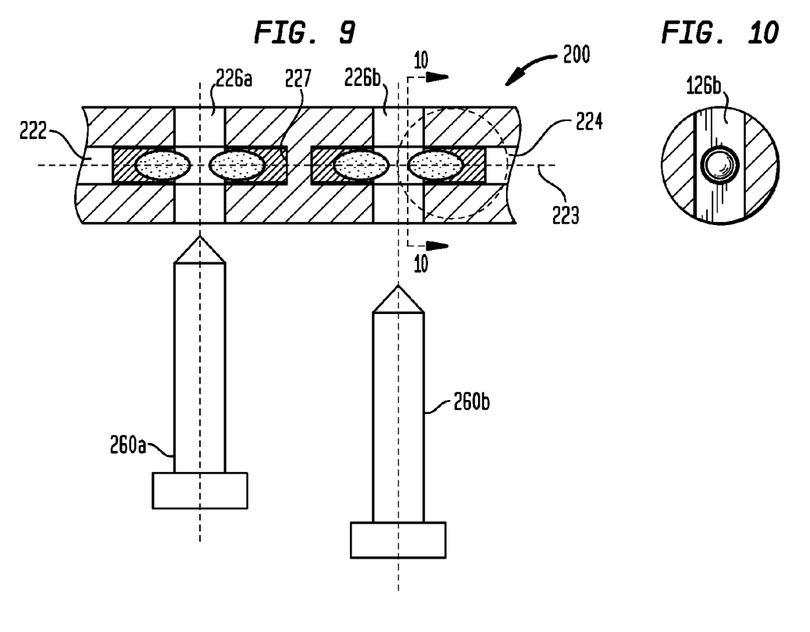
FIG. 9 is a cross-sectional view of an alternative embodiment of an intramedullary nail having a plurality of holders and adhesive capsules shown in FIG. 7 located in a longitudinal bore of the intramedullary nail.
FIG. 10 is a cross-sectional view of the intramedullary nail taken along line B-B of FIG. 9.

FIGS. 7-11 refer to screw locking system 200. Preferably screw locking system 200 includes intramedullary nail 200, at least one adhesive capsule 240, at least one capsule holder 270, and at least one fastener 260. Two fasteners 260*a*, 260*b* are shown in FIG. 9. Screw locking system 200 may also include an insertion instrument 290 for engaging and manipulating capsule holder 270.

FIGS. 7-8A show adhesive capsule 240, capsule holder 270, and insertion instrument 290. As shown in FIG. 7, adhesive capsule 240 preferably includes an outer casing 242 housing an adhesive material. The outer casing 242 of the adhesive capsule 240 is preferably thin such that it may easily be pierced by fasteners, such as fasteners 260*a*, 260*b* as shown in FIG.9, for example. Adhesive capsule 240 preferably forms chamber 244 for housing adhesive material therein. Alternatively, adhesive capsule 240 may include two or more chambers. A barrier wall may be used to separate the adhesive of capsule 240 into first and second chambers, for instance. Adhesive capsule 240 may further include more than one barrier wall to form a plurality of chambers.

In FIG. 8, insertion instrument 290 is shown in alignment with capsule holder 270 prior to being engaged to capsule holder 270 as shown in FIG. 8A. Insertion instrument 290 preferably has an engagement end 292 that is configured to engage a corresponding end 274 of capsule holder 270. The engagement between insertion instrument 290 and capsule holder 270 may occur through a press-fit, threaded engagement, or a lock-fit, such as a ball and detent connection, for example.

Holder 270 has first and second ends 271, 272, each end having a recess 276 for housing an adhesive capsule 240 therein. Recess 276 may be a bore that passes through first and second ends 271, 272 of holder 270. As shown in FIG. 8, holder 270 may include external threads 280 configured to engage corresponding threads in nail 220. Holder 270 is preferably cylindrical.

In screw locking system 200, intramedullary nail 220 is a preferably elongate shaft configured to be housed within a canal of a patient's femur. Preferably, intramedullary nail 220 includes at least two longitudinal recess or bores 222, 224 at least partially along a length thereof. In this embodiment, recess or bore 222 does not extend along a substantial length of nail 220, and is preferably interrupted by a wall 227 along the length of nail 220 separating recess 222 from recess 224. Preferably, each recess 222, 224 is shown having an axis 223. While axis 223 is shown as a straight line in FIGS. 9 and 11, axis 223 may curve if a portion of the length of nail 220 is also curved. Intramedullary nail 220 preferably further includes at least first and second bone screw receiving apertures 226a, 226b. Preferably, apertures 226a, 226b each extend transverse to recesses 222, 224 of intramedullary nail 220.

As shown in FIG. 9, a plurality of capsules 240 each housed in a holder 270 are located in recesses 222, 224 of nail 120. Holder 270 housing capsules 240 are located in recesses 222, 224 such that a portion of capsules 240 are located in fastener receiving apertures 226a, 226b of nail 220. FIG. 10A is a cross-sectional view showing capsule 240 located in recess 224, for example.

Figure 11:
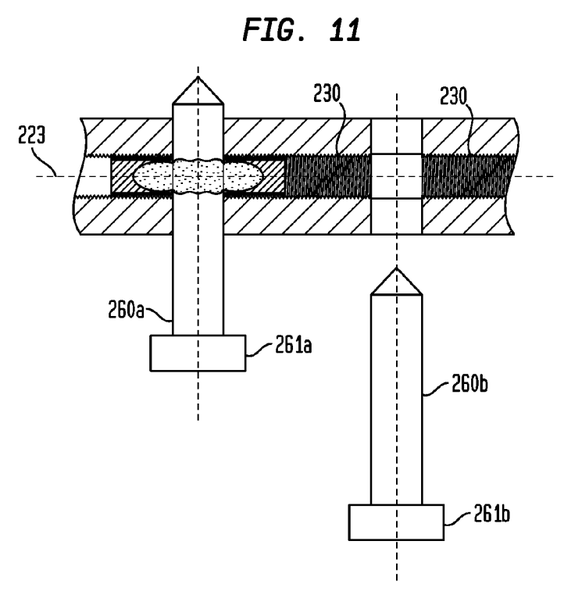
FIG. 11 is a cross-sectional view of the intramedullary nail shown in FIG. 9, with one of the plurality of adhesive capsules having been pierced by a fastener located in an aperture of the intramedullary nail.

As shown in FIG. 11, fasteners 260a has pierced adhesive capsule 240 in fastener receiving aperture 226a such that the adhesive material preferably surrounds a length of fastener 260a. Preferably, fastener 260a is received within apertures 226a until a head 261 of fastener 260a is seated on the exterior surface of the patient's bone (not shown). Depending on the chemical and physical properties of the adhesive material in adhesive capsule 240, the adhesive material will eventually harden and secure fastener 260a, for example, with respect to nail 220.

Recesses 222, 224 are shown threaded in FIG. 11, such that an insertion instrument 290 engaged to a holder 270 may be rotated to thread holder 270 into position within recesses 222, 224. Holder 270 is adapted to be received within a longitudinal bore 22, or recesses 122,124,222,224 of the elongate shaft of nail 10,100,200.

In one embodiment, nail 10 includes first and second transverse apertures 26a, 26b and holder 270 is positioned within the longitudinal bore 22 of nail 20 such that the holder 270 communicates with the first and second transverse apertures 26a, 26b, wherein the holder 270 has first and second recesses 272 each adapted to receive an adhesive capsule 40,140,240.

FIGS. 12-15 refer to screw locking system 300. Preferably screw locking system 300 includes intramedullary nail 320, at least one adhesive capsule 340, and at least one fastener 360 (not shown).

Figure 14:
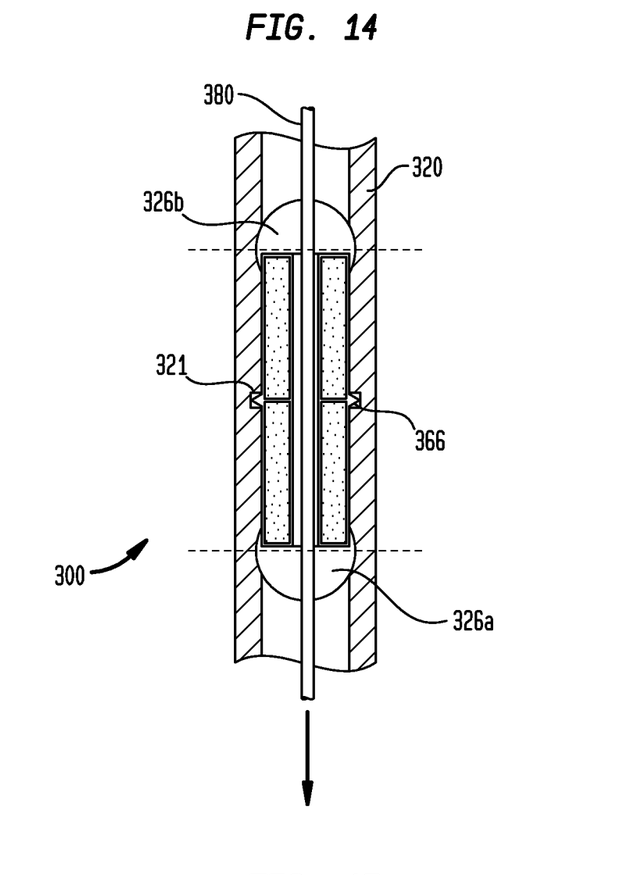
FIG. 14 is a perspective view of an intramedullary nail, guide wire, and adhesive capsule shown in FIG. 12.
Figure 15:
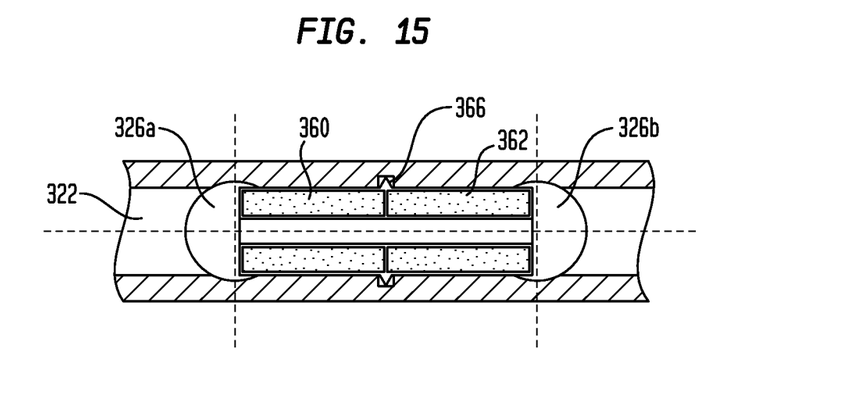
FIG. 15 is a cross-sectional view of the adhesive capsule located in the longitudinal bore of the intramedullary nail shown in FIG. 14.

Intramedullary nail 320 is a preferably elongate shaft configured to be housed within a canal of a patient's femur. Preferably, intramedullary nail 320 includes a longitudinal bore 322 at least partially along a length thereof. Longitudinal bore 322 preferably includes at least one recess 321 adapted to receive a retaining portion 366 extending from adhesive capsule 340. Intramedullary nail 320 preferably further includes at least first and second bone screw receiving apertures 326a, 326b. Preferably, apertures 326a, 326b each extend transverse to longitudinal bore 322 of intramedullary nail 320.

Figure 12:
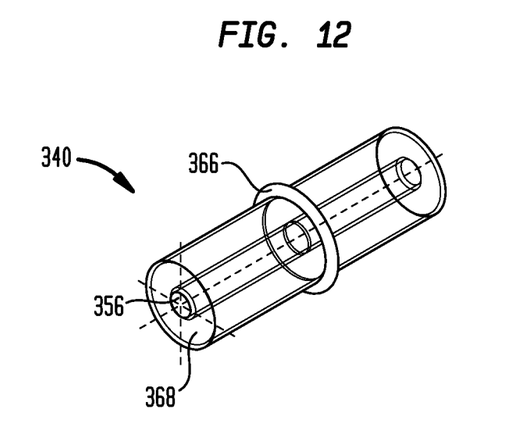
FIG. 12 is a perspective view of an alternative embodiment of an adhesive capsule.
Figure 13:
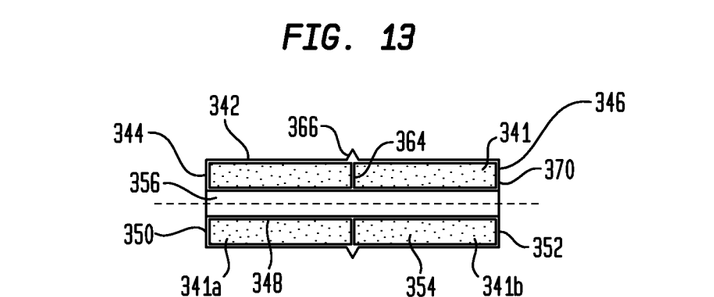
FIG. 13 is a cross-sectional view taken along the line C-C of the adhesive capsule shown in FIG. 12.

Adhesive capsule 340 preferably includes a longitudinally extending exterior wall 342 having a first end 344 and a second end 346. Adhesive capsule 340 preferably further includes a longitudinally extending interior wall 348 spaced from exterior wall 342, the interior wall 348 having a first end 350 and a second end 352. The first and second ends of the exterior and interior walls are preferably sealed, such that the sealed exterior and interior walls define an enclosed chamber 354. Preferably, an adhesive 341 is contained within enclosed chamber 354. The interior wall 348 forms a passageway 356 along a length of the adhesive capsule 340 and through the first and second ends 350, 352 of interior wall 348.

As shown in FIG. 15, the enclosed chamber 354 containing adhesive 341 preferably includes a first longitudinal section 360 and a second longitudinal section 362 separated by a barrier wall 364 such that the adhesive in the first section 341a is separated from the adhesive in the second section 342b. Preferably, barrier wall 364 is located at an intermediate portion along the length of adhesive capsule 340. Preferably, the exterior wall 342 of adhesive capsule 340 has a circumferential ridge or retaining portion 366 that extends outwardly therefrom.

Preferably, the exterior and interior walls 342, 348 of adhesive capsule 340 are substantially cylindrical and passageway 322 is substantially cylindrical such that the enclosed chamber 354 is annular.

Preferably, adhesive capsule 340 includes a first end wall 368 and a second end wall 370, wherein a first end of annular chamber 354 located at first ends 344, 350 of exterior and interior walls 342, 348 is sealed by the first end wall 368 and a second end of annular chamber 354 located at second ends 346, 352 of exterior and interior walls 342, 348 are sealed by second end wall 370.

As shown in FIGS. 14 and 15, in order to place adhesive capsule 340 in position within nail 320, a portion of a guide wire 380 is passed through passageway 356 of adhesive capsule 340. Guide wire 380 has a sufficient diameter to pass through passageway 356 while also allowing guide wire 380 to engage interior wall 348 of adhesive capsule. Once adhesive capsule 340 is engaged to guide wire 380, adhesive capsule 340 may be received in longitudinal bore 322 of nail 320. Preferably, guide wire 380 passes through longitudinal bore 322 of nail 320 until retaining ring 366 engages recess 323 of longitudinal bore 322 as shown in FIG. 14.

As shown in FIG. 15, once adhesive capsule 340 is in place, guide wire 380 may be removed from longitudinal bore 322 of nail 320 leaving behind adhesive capsule 340. Similar to the embodiment shown in FIG. 3, fasteners 360a, 360b (not shown) may be placed through apertures 326a, 326b of nail 320 respectively such that fasteners 360a, 360b pierce adhesive capsule 340. Preferably, after piercing adhesive capsule 340 with fasteners 360a, 360b, the adhesive material housed within annular chamber 341 preferably surrounds a length of fasteners 360a, 360b. Preferably, fasteners 360a, 360b are received within apertures 326a, 326b until a head 361 of each fastener is seated on an exterior surface of the patient's bone (not shown). Depending on the chemical and/or physical properties of the adhesive material located inside capsule 340, the adhesive material will eventually harden and secure fasteners 360a, 360b with respect to nail 320, thus securing nail 320 with the canal of the patient's femur.

In other embodiments, biologically active agents may be incorporated inside capsules 40, 140, 240, 340. Active agents amenable for use in capsules 40, 140, 240, 340 include growth factors, such as bisphosphonates, transforming growth factors, fibroblast growth factors, platelet derived growth factors, epidermal growth factors, connective tissue activated peptides, osteogenic factors, and biologically active analogs, fragments, and derivatives of such growth factors.

In addition to the biological active agents discussed above, a large number of pharmaceutical agents are known in the art and are amenable for use in capsule. The term "pharmaceutical agent" includes without limitation, medicaments, vitamins, mineral supplements, substances used for the treatment, prevention, diagnosis, cure or mitigation of disease or illness, or substances which affect the structure or function of the body, or prodrugs, which become biologically in a predetermined physiological environment.

Non-limiting examples of broad categories of useful pharmaceutical agents include the following therapeutic categories: anabolic agents, antacids, anti-asthmatic agents, anti-coagulants, anti-convulsants, anti-diarrheals, anti-infective agents, anti-inflammatory agents, anti-nauseants, and analgesic agents. The therapeutic agent may also be an at least one drug that is a member of a drug class selected from the group consisting of ace-inhibitors, alkaloids, anabolic agents, analgesics, antacids, anti-allergy agents, anti-Alzheimer's Disease agents, anti-anginal drugs, antianxiety agents, anti-arrhythmia agents, antiasthmatics, antibacterial agents, anti-bipolar agents, antifungal agents, antibiotics, anticholesterolemics, anticlotting agents, anticonvulsants, anticoagulants, antidepressants, antidiarrheal preparations, anti-emetics, antihistamines, antihyperglycemic agents, antihypertensives, anti-impotence agents, anti-infectives, anti-inflammatories, antilipid agents, antimanics, anti-migraine agents, antinauseants, antineoplastics, antiobesity agents, antiparasitics, anti-Parkinsonism agents, antipsychotics, antipyretics, antispasmodics, antistroke agents, antithrombotics, antithyroid preparations, antitumor agents, antitussives, antiulcer agents, anti-uricemic agents, antiviral agents, anxiolytic agents, appetite stimulants, appetite suppressants, autoimmune disorders agents, barbiturates, betablocking agents, blood glucose-lowering agents, bronchodilators, cardiovascular agents, cerebral dilators, chelating agents, cholecystekinin antagonists, chemotherapeutic agents, cholesterol-reducing agents, cognition activators, cognitive enhancers, contraceptives, coronary dilators, cough suppressants, decongestants, deodorants, dermatological agents, diabetes agents, diuretics, emollients, enzymes, erythropoietic drugs, expectorants, fertility agents, fungicides, gastrointestinal agents, growth regulators, anti-headache agents, anti-cluster headache agents, hormone replacement agents, hyperglycemic agents, hypnotic agents, hypoglycemic agents, ion-exchange resins, laxatives, migraine treatments, mineral supplements, active or more active after they have been placed mucolytics, narcotics, neuroleptics, neuromuscular drugs, non-steroidal anti-inflammatories (NSAIDs), nutritional additives, peripheral vasodilators, polypeptides, prostaglandins, psychotropics, renin inhibitors, respiratory stimulants, anti-restless leg syndrome agents, sedatives, steroids, stimulants, sympatholytics, thyroid preparations, tranquilizers, uterine relaxants, vaginal preparations, vasoconstrictors, vasodilators, vertigo agents, vitamins, wound healing agents, and combinations thereof.

The at least one drug is selected from the group consisting of acetazolamide, acetaminophen, acetic acid, acetohexamide, acetylsalicylic acid, buffered acetylsalicylic acid; acrivastine, acyclovir, albuterol, albuterol sulfate, alcohol, alfaxalone, alkaline phosphatase, allantoin, aloe, alprostadil, aluminum acetate, aluminum carbonate, aluminum chlorohydrate, aluminum hydroxide, alprozolam, amino acids, aminobenzoic acid, amlodipine besylate, amoxicillin, ampicillin, amsacrine, amsalog, anethole, apomorphine, ascorbic acid, aspartame, aspirin, astemizole, atenolol, atorvastatin calcium, azatidine, azatidine maleate, azithromycin, bacitracin, balsam peru, BCNU (carmustine), becampicillin hydrochloride, beclomethasone diproprionate, benzalkonium chloride, benzocaine, benzoic acid, benzophenones, benzoyl peroxide, benzquinamide, benzquinamide hydrochloride, betamethasone, bethanechol, biotin, bisacodyl, bismuth subsalicylate, bomyl acetate, bromopheniramine, bromopheniramine maleate, bupropion hydrochloride, buspirone, caffeine, calamine, calcium carbonate, calcium casinate, calcium hydroxide, camphor, captopril, carbenicillin indanyl sodium, carvedilol, cascara sagrada, castor oil, cefaclor, cefadroxil, celicoxib, cephalexin, centrizine, centrizine hydrochloride, cetirizine, cetyl alcohol, cetylpyridinium chloride, chelated minerals, chlorambucil, chloramphenicol, chlorcyclizine hydrochloride, chlordiazepoxide, chlorhexidine gluconate, chloroxylenol, chloropentostatin, chlorpheniramine, chlorpheniramine maleate, chlorpheniramine tannate, chlorpromazine, chlorpropamide, chlorthalidone, chlorzolamide, cholestyramine resin, choline bitartrate, chondrogenic stimulating protein, cimetidine, cimetidine hydrochloride, cinnamedrine hydrochloride, cinnarizine, cisapride, citalopram, citric acid, clarithromycin, clemastine, clemastine flumarate, clonidine, clonidine hydrochloride, clorfibrate, cocoa butter, cod liver oil, codeine, codeine fumarate, codeine phosphate, cortisone acetate; cotrimoxazole, ciprofloxacin HCl, cyanocobalamin, cyclizine hydrochloride, cyproheptadine, cyproheptadine hydrochloride, dexmethylphenidate, danthron, dexbromopheniramine maleate, dextromethorphan, dextromethorphan hydrohalide, diazepam, dibucaine, dichloralphenazone, diclofen, alkali metal salts of diclofen, diclofenac sodium, dicumarol, digitoxin, digoxin, dihydroergotamine, hydrogenates of dihydroergotamine, mesylates of dihydroergotamine, diltiazem, dimebon, dimenhydrinate, dimethicone, dioxybenzone, diphenhydramine, diphenhydramine citrate, diphenhydramine hydrochloride, divalproex, alkali metal salts of divalproex, docusate calcium, docusate potassium, docusate sodium, donepezil, doxazosin, doxepin, doxepin hydrochloride, doxycycline hydrate, doxylamine succinate, dronabinol, echinomycin, econazole, efaroxan, enalapril, enalaprilic acid, enoxacin, ephedrine, epinephrine bitartrate, ergotamine, ergotamine tartrate, erythromycin, erythropoietin, estropipate, ethinyl estradiol, etomidate, eucalyptol, famotidine, fenoprofen, metal salts of fenoprofen, ferrous fumarate, ferrous gluconate, ferrous sulfate, fluconazole, fluoxetine, fluoxymesterone, folic acid, fosphenytoin, 5-fluorouracil (5-FU), fluoxetine, fluoxetine hydrochloride, flurbiprofen, fluspirilene, furosemide, gabapentan, gentamicin, gemfibrozil, glipizide, glycerine, glyceryl stearate, granisetron, granisetron hydrochloride, griseofulvin, guafenesin, hexylresorcinol, hydrochlorothiazide, hydrocodone, tartrates of hydrocodone, hydrocortisone, hydrocortisone acetate, 8-hydroxyquinoline sulfate, hydroxyzine, hydroxyzine pamoate, hydrochloride salts of hydroxyzine, ibuprofen, indomethacin, inositol, insulin, iodine, ipecac, iron, iroxicam, isosorbide, monoand dinitrates of isosorbide, isoxicam, kaolin, ketamine, ketanserin, ketoprofen, lactic acid, lanolin, L-DOPA, lecithin, leuprolide acetate, levocabastine, lidocaine, lidocaine hydrochloride, lifinopril, liotrix, lisinopril, lomustine, loperamide, loratadine, lovastatin, magnesium carbonate, magnesium hydroxide, magnesium salicylate, magnesium trisilicate, meclizine, meclizine hydrochloride, mefenamic acid, meclofenamic acid, meclofenamate sodium, medroxyprogesterone acetate, meloxicam, memantine, methenamine mandelate, menthol, meperidine hydrochloride, metaproterenol sulfate, methanstenolone, methscopolamine, nitrates of methscopolamine, methsergide, methsergide maleate, methyl nicotinate, methyl salicylate, methyl cellulose, methsuximide, 17-methyltestosterone, metoclopramide, halides of metoclopramide, hydrates of metoclopramide, metronidazole, metronidazole hydrochloride, metoprolol, metoprotol tartrate, mianserin, miconazole nitrate, mineral oil, minocycline, minoxidil, mioflazine, morphine, nadolol, naproxen, sodium salts of naproxen, alkali metal salts of naproxen, nifedipine, neomycin sulfate, niacin, niacinamide, nicotine, nicotinamide; nimesulide; nitroglycerine; nonoxynol-9; norethindrone and its acetate; nystatin, octoxynol, octoxynol-9, octyl dimethyl PABA, octyl methoxycinnamate, omega-3 polyunsaturated fatty acids, omeprazole, ondansetron, ondansetron hydrochloride, oxfendazole, oxolinic acid, oxybenzone, oxtriphylline, para-aminobenzoic acid (PABA), padimate-O, paramethadione, paroxetine, penfluridole, penicillin G, pentastatin, peppermint oil, pentaerythritol tetranitrate, pentobarbital sodium, perphenazine, phenelzine sulfate, phenindamine, phenindamine tartrate, pheniramine maleate, phenobarbital, phenol, phenolphthalein, phenylephrine, tannates of phenylephrine, hydrochlorides of phenylephrine, phenylpropanolamine, phenylpropanolamine hydrochloride, phenyloin, pirmenol, piroxicam, salts of piroxicam, polymicin B sulfate, potassium chloride, potassium nitrate, pramipexole, pramiracetin, pramoxine, pramoxine hydrochloride, prazepam, prazosin, prednisolone, procainamide hydrochloride, procaterol, promethazine, promethazine hydrochloride, propoxyphene, propoxyphene hydrochloride, napsylate, prochlorperazine, prochlorperazine maleate, propanolol, propanolol hydrochloride, promethazine, promethazine hydrochloride, propanolol, prostacyclin, pseudoephedrine, sulfates of pseudoephedrine, hydrochlorides of pseudoephedrine, pyridoxine, pyrolamine, hydrochlorides of pyrolamine, tannates of pyrolamine, quetiapine, quinapril, quinidine gluconate, quinidine sulfate, quinestrol, ralitoline, ramipril, ranitidine, resorcinol, retinol, riboflavin, rivastigmine, rosiglitazone, salicylic acid, scopolamine, sertraline, sesame oil, shark liver oil, sildenafil citrate, simethicone, sodium bicarbonate, sodium citrate, sodium fluoride, sodium monofluorophosphate, spiramycin, spironolactone, sucralfate, sulfanethoxazole, sulfasalazine, sulfur, sulpiride, sumatriptan, sumatriptan succinate, tacrine, tacrine hydrochloride, terconazole, terfenadine, testosterone, tetracycline, tetracycline hydrochloride, tetrahydroaminoacridine, theophylline, thiabendazole, thiethylperazine, thiethylperazine maleate, thioperidone, thiothixene hydrochloride, timolol, timolol maleate, tolmetin, tolnaftate, topiramate, tramadol, tretinoin, triazolam, trimetrexate, trimazosin, triclosan, trimethobenzamide, trimethobenzamide hydrochloride, tripelennamine, tripelennamine hydrochloride, tripolidine hydrochloride, troleandomycin, tubulazole, undecylenic acid, valdecoxib, vancomycin, venlafaxine, verapamil HCl, vidaribine phosphate, virazole, vitamin A, vitamin C, vitamin D, vitamin B1, vitamin B2, vitamin B3, vitamin B4, vitamin B5, vitamin B6, vitamin B7, vitamin B9, vitamin B12, vitamin E, vitamin K, witch hazel, xylometazoline hydrochloride, zinc, zinc sulfate, zinc undecylenate, ziprasidone, zolpidem, salts thereof, and combinations thereof.

In yet further embodiments, the biologically active agents, pharmaceutical agents, and drugs discussed above may be incorporated inside capsules 40, 140, 240, 340 without any adhesive in capsules 40, 140, 240, 340.

In the embodiments where adhesives are includes in capsules 40, 140, 240, 340, various additives may be included in the inventive adhesive to adjust its property. For example, bone cements, proteins, osteoinductive and/or osteoconductive materials, X-ray opacifying agents, supporting or strengthening filler materials, crystal growth adjusters, viscosity modifiers, pore forming agents, and other additives and a mixture thereof may be incorporated without departing from the scope of this invention.

The nature of the compounds and functional materials present in the bone cements is not limited to the heretofore described ingredients, but to the contrary, any other suitable osteoconductive, bioactive, bioinert, or other functional materials may be used in conjunction with the invention. When used, these optional ingredients, may be present in any amounts suitable for their intended purposes.

In some embodiments, the bone cement includes an osteoinductive protein, by which is contemplated any protein that is useful in assisting in or inducing bone formation.

Osteoinductive proteins are deemed particularly suitable for use in conjunction with the carboxyl/calcium cement systems because, at least for many known osteoinductive proteins, such proteins may denature at an alkaline pH.

Another optional ingredient is a filler, such as a radio opaque filler. The radio opaque filler may, for instance, be a suitable bismuth, barium, or iodide compound, such as barium sulfate or bismuth hydroxide. Other suitable fillers include bioglass, silicas, alumina, biphasic calcium phosphate, calcium silicate, calcium sulfate, granular calcium phosphate ceramics, Portland cement, and the like.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:
1. A bone nail comprising:
   a shaft having a bore defining a first wall extending along at least a portion of a length thereof;
   at least one bone screw receiving aperture defining a second wall extending transverse to the first wall of the bore such that an edge is defined between the first and second walls; and
   an adhesive capsule containing an adhesive and positioned at least partially within the bore of the shaft along the first wall and adjacent the edge such that it communicates with both the first wall of the bore and the second wall of the at least one bone screw receiving aperture such that a fastener can pierce the adhesive capsule to release the adhesive to fasten the fastener to the bone nail.

2. The bone nail of claim 1, wherein the first wall of the bore is an internal wall of the shaft.

3. The bone nail of claim 2, wherein the internal wall has a longitudinal axis collinear with a central longitudinal axis of the shaft.

4. The bone nail of claim 1, further comprising:
   a holder adapted to be received at least partially within the bore of the shaft, the holder adapted to receive the adhesive capsule therein and position the adhesive capsule at least partially within the at least one bone screw receiving aperture.

5. The bone nail of claim 4, wherein the bore is threaded adjacent the at least one bone screw receiving aperture and the holder is threaded and adapted to threadingly engage the bore of the shaft.

6. The bone nail of claim 1, wherein the adhesive capsule includes at least one therapeutic agent.

7. A bone nail comprising:
   a shaft having a bore defining a first wall extending along at least a portion of a length thereof;
   first and second bone screw receiving apertures each defining a second wall and each extending transverse to the first wall of the bore such that a first edge is defined between the first wall of the bore and the second wall of the first bone screw receiving aperture and a second edge is defined between the first wall of the bore and the second wall of the second bone screw receiving aperture; and
   an adhesive capsule containing an adhesive positioned at least partially within the bore of the shaft adjacent the first and second edges such that it communicates with the bore and both the first and second bone screw receiving apertures.

8. The bone nail of claim 7, wherein the first wall of the bore is an internal wall of the shaft.

9. The bone nail of claim 8, wherein the internal wall has a longitudinal axis collinear with a central longitudinal axis of the shaft.

10. The bone nail of claim 7, further comprising:
a holder adapted to be received at least partially within the bore of the shaft, the holder adapted to receive the adhesive capsule therein and position the adhesive capsule at least partially within at least one of the first and second bone screw receiving apertures.

11. The bone nail of claim 10, wherein the bore is threaded adjacent at least one of the first and second bone screw receiving apertures and the holder is threaded and adapted to threadingly engage the bore of the shaft.

12. The bone nail of claim 7, further comprising:
a holder adapted to be received at least partially within the bore of the shaft, wherein the holder has first and second ends each having a recess to position the adhesive capsule at least partially within either the first or second bone screw receiving apertures.

13. The bone nail of claim 7, wherein the adhesive capsule includes at least one therapeutic agent.

14. A bone nail comprising:
a shaft having a bore and a first bone screw receiving aperture extending transverse to the bore;
a first adhesive capsule containing an adhesive; and
a threaded holder received within and threadingly engaged to the bore, the holder having at least one recess receiving the first adhesive capsule and positioning the first adhesive capsule at least partially within the first bone screw receiving aperture such that a fastener can pierce the first adhesive capsule to release the adhesive to fasten the fastener to the bone nail.

15. The bone nail of claim 14, wherein the bore forms an internal wall of the shaft.

16. The bone nail of claim 15, wherein the internal wall has a longitudinal axis collinear with a central longitudinal axis of the shaft.

17. The bone nail of claim 14, further comprising:
a second adhesive capsule containing an adhesive; and
a second bone screw receiving aperture extending transverse to the bore,
wherein the holder is adapted to receive the second adhesive capsule therein and position the second adhesive capsule at least partially within the second bone screw receiving aperture.

18. The bone nail of claim 17, wherein the first and second adhesives capsules each have a casing housing the adhesive.

19. the bone nail of claim 18, wherein the first and second adhesive capsules also each include at least one therapeutic agent.

* * * * *